(12) United States Patent
Mehta

(10) Patent No.: US 7,932,263 B2
(45) Date of Patent: Apr. 26, 2011

(54) THERAPEUTIC TREATMENT

(75) Inventor: Jay Lal Mehta, Little Rock, AR (US)

(73) Assignee: AstraZeneca AB, Sodertalje (SE)

( * ) Notice: Subject to any disclaimer, the term of this patent is extended or adjusted under 35 U.S.C. 154(b) by 167 days.

(21) Appl. No.: 10/573,353

(22) PCT Filed: Sep. 22, 2004

(86) PCT No.: PCT/GB2004/004120

§ 371 (c)(1),
(2), (4) Date: Jun. 8, 2007

(87) PCT Pub. No.: WO2005/030215

PCT Pub. Date: Apr. 7, 2005

(65) Prior Publication Data

US 2007/0275989 A1   Nov. 29, 2007

(30) Foreign Application Priority Data

Sep. 26, 2003 (GB) .................................. 0322552.1

(51) Int. Cl.
*A01N 43/90* (2006.01)
(52) U.S. Cl. .................. 514/279; 514/263.34; 514/263.4
(58) Field of Classification Search .................. 514/263
See application file for complete search history.

(56) References Cited

U.S. PATENT DOCUMENTS

| | | | |
|---|---|---|---|
| 5,196,444 A | 3/1993 | Naka et al. | 514/381 |
| 5,298,497 A | 3/1994 | Tschollar et al. | 514/91 |
| 5,328,919 A | 7/1994 | Naka et al. | 514/381 |
| 5,401,764 A | 3/1995 | Naka et al. | 514/381 |
| 5,703,110 A | 12/1997 | Naka et al. | 514/396 |
| 5,705,517 A | 1/1998 | Naka et al. | 514/381 |
| 5,721,263 A | 2/1998 | Inada et al. | 514/381 |
| 5,958,961 A | 9/1999 | Inada et al. | 514/394 |
| 5,962,491 A | 10/1999 | Naka et al. | 514/381 |
| 6,004,989 A | 12/1999 | Naka et al. | 514/381 |
| 6,228,874 B1 | 5/2001 | Inada et al. | 514/364 |
| 6,232,334 B1 | 5/2001 | Naka et al. | 514/381 |
| 6,348,481 B2 | 2/2002 | Inada et al. | 514/364 |
| 6,355,808 B2 | 3/2002 | Naka et al. | 548/252 |
| 6,420,405 B2 | 7/2002 | Inada et al. | 514/381 |
| 6,620,821 B2 * | 9/2003 | Robl | 514/290 |
| 6,894,058 B1 | 5/2005 | Cameron et al. | 514/275 |
| 2003/0053950 A1 * | 3/2003 | Leyland-Jones | 424/9.1 |
| 2003/0069221 A1 | 4/2003 | Kosoglou et al. | |
| 2009/0186908 A1 | 7/2009 | Cameron et al. | |

FOREIGN PATENT DOCUMENTS

| | | |
|---|---|---|
| CA | 2388818 | 4/2001 |
| EP | 0 457 514 | 11/1991 |
| EP | 0 521 471 | 1/1993 |
| EP | 0 628 313 | 12/1994 |
| EP | 0 753 301 | 1/1997 |
| EP | 1 306 088 | 5/2003 |
| EP | 1 306 089 | 5/2003 |
| EP | 1 314 425 | 5/2003 |
| EP | 1314425 A1 | 5/2003 |
| EP | 1673091 | 12/2009 |
| GB | 2361 185 | 10/2001 |
| GB | 2361 186 | 10/2001 |
| JP | 10-81633 | 3/1998 |
| JP | 2002-145770 | 5/2002 |
| JP | 2002145770 A | 5/2002 |
| WO | WO 93/08823 | 5/1993 |
| WO | WO 9526188 A | 5/1995 |
| WO | WO 95/26188 | 10/1995 |
| WO | WO 97/19917 | 6/1997 |
| WO | WO 97/37688 | 10/1997 |
| WO | WO 99/11260 | 3/1999 |
| WO | WO 99/11263 | 3/1999 |
| WO | WO 00/42024 | 7/2000 |
| WO | WO 00/45817 | 8/2000 |
| WO | WO 00/45818 | 8/2000 |
| WO | WO 00/45819 | 8/2000 |
| WO | WO 00/49014 | 8/2000 |
| WO | WO 00/50007 | 8/2000 |
| WO | WO 00/61551 | 10/2000 |
| WO | WO 01/15674 | 3/2001 |
| WO | WO 01/15744 | 3/2001 |
| WO | WO 01/28555 | 4/2001 |
| WO | WO 01/37808 | 5/2001 |
| WO | WO 01/54669 | 8/2001 |
| WO | WO 01/60804 | 8/2001 |
| WO | WO 01/72706 | 10/2001 |
| WO | WO 01/74394 | 10/2001 |
| WO | WO 01/76573 | 10/2001 |
| WO | WO 02/41895 | 5/2002 |
| WO | WO 02/058731 | 8/2002 |
| WO | WO 03/032995 | 4/2003 |

(Continued)

OTHER PUBLICATIONS

Qin et al. (Effects of the combination of an angiotensin II antagonist with an HMG-CoA reductase inhibitor in experimental diabetes, (Kidney International (2003), 64, 565-571, printed pp. 1 and 2, especially p. 1 (please see abstract).*

Chen, Jiawei et al. "Marked Upregulation of Lipoxygenase-1, a Receptor for Ox-Low-Density Lipoprotein in Atherosclerosis, and Its Total Ablation by Candesartan and Rosuvastatin Given Concurrently", Journal of American College of Cardiology, vol. 43, No. 5 (Supplement A) Mar. 3, 2004 p. 498A, (Abstract).

Qin et al. "Effects of the combination of an angiotensin II antagonist with an HMG-CoA reductase inhibitor in experimental diabetes" Kidney International 64:565-571 (2003).

Beaudeux et al. "The Potential Role of Matrix Metalloproteinases in the Treatment of Atherosclerosis" Annales de Biologie Clinique 61: 147-158 (2003).

(Continued)

*Primary Examiner* — Sreeni Padmanabhan
*Assistant Examiner* — Timothy E Betton
(74) *Attorney, Agent, or Firm* — Morgan, Lewis & Bockius LLP

(57) ABSTRACT

A combination comprising candesartan and rosuvastatin for the prevention or treatment of arteriosclerosis and for the prevention of cardiovascular events is described.

5 Claims, 1 Drawing Sheet

FOREIGN PATENT DOCUMENTS

| | | |
|---|---|---|
| WO | WO 2004/096810 | 11/2004 |
| WO | WO 2004096810 A | 11/2004 |
| WO | WO 2004/108691 | 12/2004 |
| WO | WO 2005/023779 | 3/2005 |
| WO | WO 2005/028450 | 3/2005 |
| WO | WO 2005/030215 | 4/2005 |
| WO | WO 2005/039638 | 5/2005 |
| WO | WO 2005/042522 | 5/2005 |
| WO | WO 2006/040085 | 4/2006 |

OTHER PUBLICATIONS

Bellosta et al. "HMG-CoA Reductase Inhibitors Reduce MMP-9 Secretion by Macrophages" Arteriosclerosis, Thrombosis, and Vascular Biology 18: 1671-1678 (1998).

Bocan et al. "The ACAT Inhibitor Avasimibe Reduces Macrophages and Matrix Metalloproteinase Expression in Atherosclerotic Lesions of Hypercholesterolemic Rabbits" Arteriosclerosis, Thrombosis, and Vascular Biology 20: 70-79 (2000).

Bocan, T. "Pleiotropic Effects of HMG-CoA Reductase Inhibitors" Current Opinion in Investigational Drugs 3(9:) 1312-1317(2002).

Borghi, C. "Interactions Between Hyopercholesterolemia and Hypertension: Implications for Therapy" Current Opinion in Nephrology and Hypertension 11: 489-496 (22).

Borghi et al. "Use of Lipid-Lowering Drugs and Blood Pressure Control in Patients with Arterial Hypertension" The Journal of Clinical Hypertension 4 (4): 277-285 2002.

Brizzi et al. "Interleukin-3 Stimulates Migration and Proliferation of Vascular Smooth Muscle Cells: A Potential Role in Atherogenesis" Circulation 103: 549-554 (2001).

Chen et al. "Attenuation of Tissue P-Selectin and MCP-1 Expression and Intimal Proliferation by AT Receptor Blockade in Hyperlipidemic Rabbits" Biochemical and Biophysical Research Communications 282:474-479 (2001).

Chen et al. "Cross-Talk Between Dyslipidemia and Renin-angiotensin System and the Role of LOX-1 and MAPK in Atherogenesis Studies With the Combined Use of Rosuvastatin and Candesartan" Atherosclerosis 184 295-301 (2006).

Chen et al. "Direct Effects of Statins on Cells Primarily Involved in Atherosclerosis" Hypertension Research 23: 187-192 (2000).

Chen et al. "Inhibitory Effect of Candesartan and Rosuvastatin on CD40 and MMPs Expression in Apo-E Knockout Mice" J Cardiovasc Pharmacol 44 (4): 446-452 (2004).

Chen et al. "Interaction of Oxidized Low-density Lipoprotein and the Renin-Angiotensin System in Coronary Artery Disease" Current Hypertension Reports 8: 139-143 (2006).

Chen et al. "Marked Upregulation of Lipoxygenase-1, a Receptro for Ox-Low-Density Lipoprotein in Atherosclerosis, and Its Total Ablation by Candesartan and Rosuvastatin Given Concurrently" Journal of the American College of Cardiology 1122-166 498A (2004).

Chen et al. "Modulation of Matrix Metalloproteinase-1, Its Tissue Inhibitor, and Nuclear Factor-kB by Losartan in Hypercholesterolemic Rabbits" Journal of Cardiovascular Pharmacology 39: 332-339 (2002).

Chen et al. "Preservation of Endogenous Antioxidant Activity and Inhibition of Lipid Peroxidation as Common Mechanisms of Antiatherosclerotic Effects of Vitamin E, Lovastatin and Amlodipine" Journal of the American College of Cardiology 30: 569-575 (1997).

Chen et al. "Upregulation of LOX-1 Expression in Aorta of Hypercholesterolemic Rabbits: Modulation by Losartan" Biochemical and Biophysical Research Communications 276: 1100-1104 (2000).

Chiariello, et al. "A Biochemical Method for the Quantitation of Myocardial Scfarring after Experimental Coronary Artery Occlusion" J Mol Coll Cardiol 18: 283-290 (1986).

Chobanian et al. "Influence of Hypertension on Aortic Atherosclerosis in the Wantanabe Rabbit" Hypertension 14: 203-209 (1989).

Crisby et al. "Pravastatin Treatment Increases Collagen Content and Decreases Lipid Content, Inflammation, Metalloproteinases, and Cell Death in Human Carotid Plaques: Implications for Plaque Stabilization" Circulation 103: 926-933 (2001).

Cyrus et al. "Lipid Peroxidation and Platelet Activation in Murine Atherosclerosis" Circulation 104: 1940-1945 (2001).

J.E. Deanfield "Targeting the Atherosclerotic Process in Clinical Practice. A New Look at Established Agents" Atherosclerosis 165 189-190 (2002).

Faggiotto et al. "Statins and Blockers of the Renin-Angiotensin System Vascular Protection Beyond Their Primary Mode of Action" Hypertension 34 (part 2): 987-996 (1999).

Faia et al. "Matrix Metalloproteinases and Tissue Inhibitors of Metalloproteinases in Hamster Aortic Atherosclerosis: Correlation with In-Situ Zymography" Atherosclerosis 160: 325-337 (2002).

Ferrario et al. "The Hypertension-Lipid Connection: Insights Into the Relation Between Angiotensin II and Cholesterol in Atherogenesis" American Journal of the Medical Sciences 323 (1): 17-24 (2002).

Funakoshi et al. "Rho-Kinase Mediates Angiotensin II-Induces Monocyte Chemoattractant Protein-1 Expression in Rat Vascular Smooth Muscle Cells" Hypertension 38 100-104 (2001).

Gadddam et al. "Anti-thrombotic Effects of Atorvastatin—An Effect Unrelated to Lipid Lowering" J Cardiovasc Pharmacol Therapeut 7 (4): 247-253 (2002).

Gennaro et al. "Role of p44/p42 MAP Kinase in the Age-Dependent Increase in Vascular Smooth Muscel Cell Proliferation and Neointimal Formation" Arteriosclerosis, Thrombosis, and Vascular Biology 23: 204-210 (2003).

Goetze et al. "TNF Induces Expression of Transcription Factors c-fos, Egr-1, and Ets-1 in Vascular Lesions Through Extracellular Signal-Regulated Kinases ½" Atherosclerosis 159: 93-101 (2001).

Han et al. "Evidence for Apoptosis in Human Atherogenesis and in a Rat Vascular Injury Model" American Journal of Pathology 147: 267-277 (1995).

Hayek et al. "The Engiotensin-Converting Enzyme Inhibitor, Fosinopril, and athe Angiotensin II Receptor Antagonist, Losartan, Inhibit LDL Oxidation and Attenuate Atherosclerosis Independent of Lowering Blood Pressure in Apolipoprotein E Deficient Mice" Cardiovascular Research 44: 579-587 (1999).

Holman et al. "Technics for Studying Atherosclerotic Lesions" Laboratory Investigation 7 42-47 (1958).

Horton et al. "Ligation of CD40 on Vascular Smooth Muscle Cells Mediates Loss of Interstitial Collagen via Matrix Metalloproteinase Activity" Annals of New York Academy of Sciences 947: 329-336 (2001).

Hu et al. "Hyperexpression and Activation iof Extracellular Signal-Regulated Kinases (Erk½) in Atherosclerotic Lesion of Cholesterol-Fed Rabbits" Arteriosclerosis, Thrombosis, and Vascular Biology 20: 18-26 (2000).

Ikeda et al. "Monocyte-Endothelial Cell Interaction in Atherogenesis and Thrombosis" Clin. Cardiol. 21 11-14 (1998).

Ikeda et al. "Statins and Monocytes" The Lancet 353: 2070 (1999).

Ito et al. "Novel Mechanism for Endothelial Dysfunction: Dysregulation of Dimethylarginine Dimethylaminohydrolase" Circulation 99: 3092-3095 (1999).

Iwai-Kanai et al. "Activation of Lectin-Like Oxidized Low-Density Lipoprotein Receptor-1 Induces Apoptosis in Cultured Neonatal Rat Cardiac Myocytes" Circulation 104: 2948-2954 (2001).

Jacobsson et al. "Antiatherosclerotic Effects of the Angiotensin-Converting Enzyme Inhibitors Captopril and Fosinopril in Hypercholesterolemic Minipigs" Journal of Cardiovascular Pharmacology 24: 670-677 (1994).

Jacoby et al. "Renin-Angiotensin System and Atherothrombotic Disease" Arch Intern Med 163 1155-1164 (2003).

Jing et al. "Activation of p38 Mitogen—Activated Protein Kinase by Oxidized LDL in Vascular Smooth Muscle Cells: Mediation via Pertussis Toxin-Sensitive G Proteins and Association With Oxidized LDL-Induced Cytotoxicity" Circulation Research 84: 831-839 (1999).

Kaneko et al. Chemical Abstracts 118(11) (1993).

Keidar et al. "Angiotensin II Injection into Mice Increases the Uptake of Oxidized LDL by Their Macrophages via a Proteoglycan-Mediated Pathway" Biochemical and Biophysical Research Communications 239: 63-67 (1997).

Keidar et al. "Angiotensis II Stimulates Macrophage-Mediated Oxidation of Low Density Lipoproteins" Atherosclerosis 115: 201-215 (1995).

Knox et al. "Evidence for Altered Balance between Matrix Metalloproteinases and Their Inhibitors in Human Aortic Diseases" Circulation 95: 205-212 (1997).

Lacoste et al. "Hyperlipidemia and Coronary Disease" Circulation 92 (31) 3172-3177 (1995).

Li et al. "Angiotensin II via Activation of Type 1 Receptor Upregulates Expression of Endoglin in Human Coronary Artery Endothelial Cells" Hypertension 38: 1062-1067 (2001).

Li et al. "LOX-1 Inhibition in Myocardial Ischemia-Reperfusion Injury: Modulation of MMP-1 and Inflammation" Am J Physiol Heart Circ Physiol 283: H1795-H1801 (2002).

Li et al. "LOX-1 Mediates Oxidized Low-Density Lipoprotein-Induced Expression of Matrix Metalloproteinases in Human Coronary Artery Endothelial Cells" Circulation 107: 612-617 (2003).

Li et al. "Modulation of Constitutive Nitric Oxide Synthase, bc1-2 and Fas Expression in Cultured Human Coronary Endothelial Cells Exposed to Anoxia-Reoxygenation and Angiotensin II: Role of AT1 Receptor Activation" Cardiovascular Research 41: 109-115 (1999).

Li et al. "Oxidized-LDL Through LOX-1 Increases the Expression of Angiotensin Converting Enzyme in Human Coronary Artery Endothelial Cells" Cardiovascular Research 57: 238-243 (2003).

Li et al. "Oxidized LDL Upregulates Angiotensin II Type 1 Receptor Expression in Cultured Human Coronary Artery Endothelial Cells" Circulation 102: 1970-1976 (2000).

Li et al. "Statins Inhibit Oxidized-LDL-Mediated LOX-1 Expression, Uptake of Oxidized-LDL and Reduction in PKB Phosphorylation" Cardiovascular Research 52: 130-135 (2001).

Li et al. "Statins Modulate Oxidized Low-Density Lipoprotein-Mediated Adhesion Molecule Expression in Human Coronary Artery Endothelial Cells: Role of LOX-1" Journal of Pharmacology and Experimental Therapeutics 302:601-605 (2002).

Li et al. "Upregulation of Endothelial Receptor for Oxidized Low-Density Lipoprotein (LOX-1) in Cultured Human Coronary Artery Endothelial Cells by Angiotensin II Type 1 Receptor Activation" Circulation Research 84: 1043-1049 (1999).

H. R. Lijnen "Non-Haemostatic Role for blood Coagulation Proteases and Their Receptors" Biochemical Society 163-167 (2002).

Manning et al. "Differential Effects of Doxycycline, a Broad-Spectrum Matrix Metalloproteinase Inhibitor, on Angiotensin II-Induced Atherosclerosis and Abdominal Aortic Aneurysms" Arteriosclerosis, Thormbosis, and Vasular Biology 23: 483-488 (2003).

Menges et al. "Oxidative Degradation of y-Butyrolactons into 1,3-Diols via a Criegee Rearrangement of Peroxosulfonates. An Enantioselective Synthesis of Capactin Lactone and its Diatereomer" Synlett 901-905 (1993).

Mehta et al. "Angiotensin II and IV Stimulate Expression and Release of Plaminogen Activator Inhibitor-1 in Cultured Human Coronary Artery Endothelial Cells" Journal of Cardiovascular Pharmacology 39: 789-794 (2002).

J.L. Mehta "Critical Role of Dyslipidemia and Angiotensin II in Atherogenesis. In: Molecular Mechanisms in Hypertension" R Re, D DiPette, E Schiffrin, J Sowers, Taylor & Francis, London (2006).

M. H. Moghadasian "Clinical Pharmacology of 3-Hydroxy-3-Methylglutaryl Coenzyme A Reductase Inhibitors" Life Sciences 65 (13): 1329-1337 (1999).

Morikawa et al. "The Effect of Statins on mRNA Levels of Genes Related to Inflammation, Coagulation, and Vascular Constriction in HUVEC" Journal of Atherosclerosis and Thrombosis 9 (4): 178-183 (2002).

Nahmod et al. "Control of Dendritic Cell Differentiation by Angiotensin II" FASEB Journal 17: 491-493 (2003).

Noji et al. "Circulating Matrix Metalloproteinases and Their Inhibitors in Premature Coronary Atherosclerosis" Clin Chem Lab Med 39 (5): 380-384 (2001).

Notarbartolo et al. "Inhibition of Thromboxane Biosynthesis and Platelet Function by Simvastatin in Type IIa Hypercholesterolemia" Arteriosclerosis, Thrombosis, and Vasculr Biology 15: 247-251 (1995).

Palinsky et al. "ApoE-Deficient Mice Are a Model of Lipoprotein Oxidation in Atherogenesis. Demonstration of Oxidation-Specific Epitopes in Lesions and High Titers of Autoantibodies to Malondialdehyde-Lysine in Serum" Arteriosclerosis, Thrombosis, and Vascular Biology 14: 605-616 (1994).

R. P. Phipps "Atherosclerosis: The Emerging Role of Inflammation and the CD40-CD40 Ligand System" PNAS 97 (13): 6930-6932 (2000).

Pullen et al. "CD40 Signaling Through Tumor Necrosis Factor Receptor-Associated Factros (TRAFs)" The Journal of Biological Chemistry 274 (20): 14246-14254 (1999).

Ramos et al. "Direct Demonstration of P-Selectin- and VCAM-1-Dependent Mononuclear Cell Rolling in Early Atherosclerotic Lesions of Apolipoprotein E-Deficient Mice" Circulation Research 84: 1237-1244 (1999).

Rosenson et al. "Statin Use in Acute Coronary Syndromes: Cellular Mechanisms and Clinical Evidence" Current Opinion Lipidol 13: 625-630 (2002).

Rouis et al. "Adenovirus-Mediated Overexpression of Tislsue Inhibitor of Metalloproteinase-1 reduces Atherosclerotic Lesions in Apolipoprotein E-Deficient Mice" Circulation 100: 533-540 (1999).

Sakaki, et al. "Lipase-catalyzed Asymmetric Synthesis of 6-(3-Chloro-2-hydroxypropy1)-1,3-dioxin-4-ones and Their Conversion of Chral 5,6-Epoxyhexanoates1" Tetrahedron Asymmetry 2(5): 343-346 (1991).

Schönbeck et al. "CD40 Signaling and Plaque Instability" Circulation Research 89: 1092-1103 (2001).

Schönbeck et al. "Expression of Stromelysin-3 in Atheroscleroticf Lesions: Regulation via CD40-CD40 Ligand Signaling In Vitro and In Vivo" J. Exp. Med. 189: (5) 843-853 (1999).

Schönbeck et al. "Inhibition of CD40 Signaling Limits Evolution of Established Atherosclerosis in Mice" PNAS 97 (13): 7458-7463 (2000).

Schönbeck et al. "Oxidized Low-Density Lipoprotein Augments and 3-Hydroxy-3-Methylglutaryl Coenzyme A Reductase Inhibitors Limit CD40 and CD4OL Expression in Human Vascular Cells" Circulation 106: 2888-2893 (2002).

Semb et al. "Raised Serum Levels of Soluble CD40 Ligand in Patients With Familial Hypercholesterolemia: Downregulatroy Effect of Statin Therapy" Journal of the American College of Cardiology 41 (2): 275-279 (2003).

Shao et al. "Asymmetric Hydrogenation of 3,5-Dioxoesters Catalyzed by Ru-binap Complex: A Short Seep Asymmetric Synthesis of 6-Substituted 5,6-dihydro-2-pyrones" Tetrahedron 49(10): 1997-2010 (1993).

Singh et al. "Interactions Between the Renin-Angiotensin System and Dyslipidemia: Relevance in Atherogenesis and Therapy of Coronary Heart Disease" Indian Heart J 53: 511-518 (2001).

Singh et al. "Interactions Between the Renin-Angiotensin System and Dyslipidemia" Arch Intern Med 163: 1296-1304 (2003).

Strawn et al. "Inhibition of Early Atherogenesis by Losartan in Monkeys With Diet-Induced Hypercholesterolemia" Circulation 101: 1586-1593 (2000).

Tamarat et al. "Angiotensin II Angiogenic Effect In Vivo Involves Vascular Endothelial Growth Factor- and Inflammation-Related Pathways" Laboratory Investigation 82 (6): 747-756 (2002).

Tayeh et al. "Angiotensin II and Bradykinin Regulate the expression P-Selectin on the Surface of Endothelial Cells in Culture" Proceedings of the Association of American Physicians 110 (5): 412-421 (1998).

Wantanabe, et al. "Antioxidant N-Acetylcysteine Inhibits Vasoactive Agents-Potentiated Mitogenic Effect of Mildly Oxidized LDL on Vascular Smooth Muscle Cells" Hypertension Research— Clinical & Experimental 25: 311-315 (2002).

Wantanabe, et al. "Synthesis and Biological Activity of Methanesulfonamide Pyrimidine- and N-Methanesulfonyl Pyrrole-Substituted 3,5-Dihydroxy-6-Heptenoates, a Novel Series of HMG-CoA Reductase Inhibitors" Bioorganic & Medicinal Chemistry 5 (2): 437-444 (1997).

Werle, et al. "MCP-1 Induces Activation of MAP-Kinases ERK, JNK and p38 MAPK in Human Endothelial Cells" Cardiovascular Research 56: 284-292 (2002).

Yang et al. "Increase in Angiotensin II Type 1 Receptor Expression Immediately After Ischemia-Reperfusion in Isolated Rat Hearts" Circulation 96: 922-926 (1997).

Yang et al. "Increased Angiotensin II Type 1 Receptor Expression in Hypercholesterolemic Atherosclerosis in Rabbits" Aterioscler Thromb Vasc Biol 18: 1433-1439 (1998).

* cited by examiner

\* P<0.01 vs control
\# P<0.05 vs HC diet
† P<0.01 vs HC diet
‡ P<0.02 vs HC diet with rosuvastatin or candesartan
n=5

1. Control mice fed with regular diet
2. Apo-E KO mice fed with HC diet
3. Apo-E KO mice fed with HC diet together with rosuvastatin
4. Apo-E KO mice fed with HC diet together with candesartan
5. Apo-E KO mice fed with HC diet together with rosuvastatin and candesartan

SEQUENCE LISTING

<160> NUMBER OF SEQ ID NOS: 12

<210> SEQ ID NO 1
<211> LENGTH: 20
<212> TYPE: DNA
<213> ORGANISM: Artificial
<220> FEATURE:

<223> OTHER INFORMATION: Synthetic sequence

<400> SEQUENCE: 1
ttactctcca tggtggtgcc                                               20

<210> SEQ ID NO 2
<211> LENGTH: 20
<212> TYPE: DNA
<213> ORGANISM: Artificial
<220> FEATURE:
<223> OTHER INFORMATION: Synthetic sequence

<400> SEQUENCE: 2
agcttcttct gcttgttgcc                                               20

<210> SEQ ID NO 3
<211> LENGTH: 20
<212> TYPE: DNA
<213> ORGANISM: Artificial
<220> FEATURE:
<223> OTHER INFORMATION: Synthetic sequence

<400> SEQUENCE: 3
gtttaaagtc ccggatgcga                                               20

<210> SEQ ID NO 4
<211> LENGTH: 20
<212> TYPE: DNA
<213> ORGANISM: Artificial
<220> FEATURE:
<223> OTHER INFORMATION: Synthetic sequence

<400> SEQUENCE: 4
ctcaaggcta tgctgtctgt                                               20

<210> SEQ ID NO 5
<211> LENGTH: 22
<212> TYPE: DNA
<213> ORGANISM: Artificial
<220> FEATURE:
<223> OTHER INFORMATION: Synthetic sequence

<400> SEQUENCE: 5
ggactctccc attcttaatg at                                            22

<210> SEQ ID NO 6
<211> LENGTH: 25
<212> TYPE: DNA
<213> ORGANISM: Artificial
<220> FEATURE:
<223> OTHER INFORMATION: Synthetic sequence

<400> SEQUENCE: 6
cctctttctg gataacatca tcaac                                         25

<210> SEQ ID NO 7
<211> LENGTH: 19
<212> TYPE: DNA
<213> ORGANISM: Artificial
<220> FEATURE:
<223> OTHER INFORMATION: Synthetic sequence

<400> SEQUENCE: 7
atcaagggga tccaggagc                                                19

<210> SEQ ID NO 8

-continued

```
<211> LENGTH: 19
<212> TYPE: DNA
<213> ORGANISM: Artificial
<220> FEATURE:
<223> OTHER INFORMATION: Synthetic sequence

<400> SEQUENCE: 8
gcagcgatga agatgatag                                            19

<210> SEQ ID NO 9
<211> LENGTH: 20
<212> TYPE: DNA
<213> ORGANISM: Artificial
<220> FEATURE:
<223> OTHER INFORMATION: Synthetic sequence

<400> SEQUENCE: 9
agtttggtgt cgcggagcac                                           20

<210> SEQ ID NO 10
<211> LENGTH: 20
<212> TYPE: DNA
<213> ORGANISM: Artificial
<220> FEATURE:
<223> OTHER INFORMATION: Synthetic sequence

<400> SEQUENCE: 10
tacatgagcg cttccggcac                                           20

<210> SEQ ID NO 11
<211> LENGTH: 20
<212> TYPE: DNA
<213> ORGANISM: Artificial
<220> FEATURE:
<223> OTHER INFORMATION: Synthetic sequence

<400> SEQUENCE: 11
ttctacaatg agctgcgttg                                           20

<210> SEQ ID NO 12
<211> LENGTH: 21
<212> TYPE: DNA
<213> ORGANISM: Artificial
<220> FEATURE:
<223> OTHER INFORMATION: Synthetic sequence

<400> SEQUENCE: 12
cactgtgttg gcatagaggt c                                         21
```

THERAPEUTIC TREATMENT

SEQUENCE LISTING SUBMISSION VIA EFS-WEB

A computer readable text file, entitled "056291-5246-SeqListing.txt," created on or about Nov. 11, 2010 with a file size of about 3 kb contains the sequence listing for this application and is hereby incorporated by reference in its entirety.

The present invention relates to a combination comprising candesartan and rosuvastatin.

The present invention further relates to pharmaceutical compositions comprising the combination mentioned hereinbefore. The present invention further relates to the use of a combination mentioned hereinbefore in the prevention or treatment of atherosclerosis.

Atherosclerosis is a condition mediated by complex pathological processes which result in irregularly distributed lipid deposits in the arteries and is a major contributory factor to coronary heart disease. A reduction in atherosclerosis is therefore a major target for reducing the number of cardiovascular events for example, myocardial infarction, worsening of angina, cardiac arrest, stroke, congestive heart failure and cardiovascular death.

Dyslipidemia, particularly increased plasma level of low-density lipoprotein (LDL) is one of the major risk factors in atherosclerosis. Clinical studies have demonstrated that reducing plasma LDL level with 3-hydroxy-3-methylglutaryl coenzyme A (HMG CoA) reductase inhibitors, commonly known as statins, results in a lower risk of cardiovascular events.

Activation of the renin-angiotensin system (RAS) may be considered another important risk factor in atherosclerosis. Activation of RAS with the formation of angiotensin (II) (A (II)) and the activation of A (II) receptors have been implicated in atherogenesis, plaque rupture, myocardial ischemic dysfunction and congestive heart failure (Singh and Mehta, Arch Intern Med, 2003, vol 163, 1296-1304).

International Patent Application WO 95/26188 discloses treatment of atherosclerosis with A(II) receptor blockers, optionally in combination with HMGCoA reductase inhibitors. International Patent Application WO 01/76573 discloses the use of a combination of at least two of an A(II) antagonist, an ACE (angiotensin converting enzyme) inhibitor and an HMGCoA reductase inhibitor for the prevention or delay of progression in a list of conditions, amongst which is atherosclerosis.

We have surprisingly found that the combination of the A(II) antagonist candesartan and the HMG CoA reductase inhibitor rosuvastatin has a synergistic effect in the reduction of atherosclerosis. This synergistic effect appears to arise from synergistic inhibition of expression of a number of inflammatory mediators involved in the RAS (for example CD40, metalloproteinases (MMPs)) and/or inhibition of the expression of the receptor LOX-1 (which is a receptor for oxidised LDL on endothelial cells). The synergistic effect provides strong evidence for cross-talk between the RAS and dyslipidemia in atherogenesis.

Figure 1:
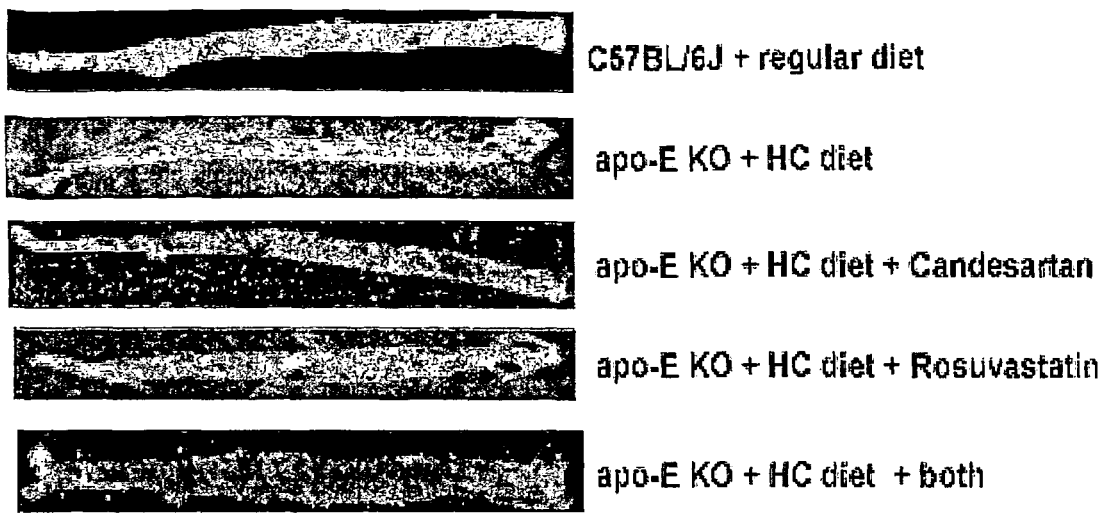
FIG. 1 shows the extent of atherosclerosis from representative comparative experiments using control mice fed with a regular diet and apo-E knockout mice fed with a high cholesterol diet, or a high cholesterol diet and administered candesartan or rosuvastatin or a combination of candesartan and rosuvastatin.

It will be appreciated that the activity of MMPs may be regulated in-vivo by their tissue inhibitors (TIMPs). We have also shown that the expression of TIMP-1 and TIMP-2 is up-regulated by high-cholesterol diet, and markedly attenuated by the combination of candesartan and rosuvastatin. These data lend credence to the concept that the balance between MMPs and TIMPs is altered by high-cholesterol diet, and that this imbalance can be "normalized" by the combination of an A(II) antagonist and a lipid-lowering agent.

In one aspect of the invention is provided a combination comprising candesartan, or a pharmaceutically acceptable salt thereof, and rosuvastatin, or a pharmaceutically acceptable salt thereof, for the prevention or treatment of atherosclerosis.

In one aspect of the invention is provided a combination comprising candesartan, or a pharmaceutically acceptable salt thereof, and rosuvastatin, or a pharmaceutically acceptable salt thereof, for the prevention of cardiovascular events.

Such a combination may also be useful in the treatment or prevention of other diseases associated with these mediators, for example in inflammatory diseases or conditions, such as ischemia-reperfusion injury (to the heart, brain, kidneys, lungs and liver), radiation-induced injury, burn injury and peripheral vascular disease, Candesartan may suitably be in the form of candesartan, or in the pro-drug form candesartan cilexetil. These forms may be formulated with a further agent such as a diuretic such as hydrochlorothiazide (for example, as marketed as Atacand Plus™).

Where herein candesartan is referred to, this includes both candesartan and candesartan cilexetil.

Preferably the calcium salt of rosuvastatin, which may be referred to as rosuvastatin calcium, is used in the various aspects of the present invention.

In general, pharmaceutically-acceptable salts include acid addition salts such as methanesulfonate, tosylate, α-glycerophosphate, fumarate, hydrochloride, citrate, maleate, tartrate and (less preferably) hydrobromide. Pharmaceutically-acceptable salts in general also include salts formed with phosphoric and sulfuric acid. Pharmaceutically-acceptable salts generally include base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine, tris-(2-hydroxyethyl)amine, tris(hydroxymethyl)methylammonium, N-methyl d-glucamine and amino acids such as lysine. There may be more than one cation or anion depending on the number of charged functions and the valency of the cations or anions.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should be such that both agents are present in the body so as to produce the synergistic effect of the combination.

In a further aspect of the invention is provided a pharmaceutical composition which comprises candesartan, or a pharmaceutically acceptable salt thereof, and rosuvastatin, or a pharmaceutically acceptable salt thereof, in association with a pharmaceutically acceptable diluent or carrier for use in the prevention or treatment of atherosclerosis.

In a further aspect of the invention is provided a pharmaceutical composition which comprises candesartan, or a pharmaceutically acceptable salt thereof, and rosuvastatin, or a pharmaceutically acceptable salt thereof, in association with a pharmaceutically acceptable diluent or carrier for use in the prevention or reduction of risk of cardiovascular events.

The compositions described herein may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream, for rectal administration for example as a suppository or the route of administration may be by direct injection into the tumour or by regional delivery or by local delivery. In other embodiments of the present invention the compounds of the combination treatment may be delivered endoscopically, intratracheally, intralesionally, percutaneously, intravenously, subcutaneously, intraperitoneally or intratumourally. In general the compositions described herein may be prepared in a conventional manner using conventional excipients or carriers that are well known in the art.

Suitable pharmaceutically-acceptable excipients or carriers for a tablet formulation include, for example, inert excipients such as lactose, sodium carbonate, calcium phosphate or calcium carbonate, granulating and disintegrating agents such as corn starch or alginic acid; binding agents such as gelatin or starch; lubricating agents such as magnesium stearate, stearic acid or talc; preservative agents such as ethyl or propyl 4-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case using conventional coating agents and procedures well known in the art.

Compositions for oral use may be in the form of hard gelatin capsules in which the active ingredient is mixed with an inert solid excipient, for example, calcium carbonate, calcium phosphate or kaolin, or as soft gelatin capsules in which the active ingredient is mixed with water or an oil such as peanut oil, liquid paraffin or olive oil.

Candesartan is commercially available as 'Atacand™' and 'Atacand Plus™'. Rosuvastatin calcium is commercially available as 'Crestor™'. Suitable formulations for the present invention include those which are commercially available.

Suitable dosages of each component of the combination are those of the marketed commercial products. Alternatively, the synergy between the components may allow a lower dosage of one or both components to be used. For example, a dose of 4 mg, 8 mg, 16 mg, 32 mg, or up to 160 mg of candesartan in combination with a dose of 80 mg, 40 mg, 20 mg, 10 mg, 5 mg or 2.5 mg of rosuvastatin may be used. It will be understood that any one of the doses of candesartan may be combined with any suitable dose of rosuvastatin.

In one aspect, 80 mg of rosuvastatin is used. In another aspect, 40 mg of rosuvastatin is used. In a further aspect, 20 mg of rosuvastatin is used. In a further aspect, 10 mg of rosuvastatin is used. In a further aspect, 5 mg of rosuvastatin is used. In a further aspect, 2.5 mg of rosuvastatin is used.

In one aspect, between 32 and 160 mg, such as about 64 to 128 mg, for example 64 to 112 mg, such as about 64-96 mg of candesartan is used. Conveniently, about 72 mg of candesartan is used. In another aspect, 32 mg of candesartan is used. In a further aspect, 16 mg of candesartan is used. In a further aspect, 8 mg of candesartan is used. In a further aspect, 4 mg of candesartan is used.

It will be appreciated that the pharmaceutical composition according to the present invention includes a composition comprising candesartan or a pharmaceutically acceptable salt thereof and rosuvastatin or a pharmaceutically acceptable salt thereof and a pharmaceutically-acceptable excipient or carrier. Such a composition, for example in a single oral formulation conveniently provides the therapeutic combination product of the invention for simultaneous administration in the prevention or treatment of atherosclerosis.

Preferably the two components of the combination are both administered orally.

Preferably the two components of the combination are administered as a single oral formulation.

Preferably the combination is formulated for once-a-day dosing.

Conveniently, the combination is formulated as a single tablet or capsule.

The dosages and schedules described hereinbefore may be varied according to the particular disease state and the overall condition of the patient. For example, it may be necessary or desirable to reduce the above-mentioned doses of the components of the combination treatment in order to reduce toxicity. Dosages and schedules may also vary if, in addition to a combination treatment of the present invention, one or more additional chemotherapeutic agents are used. Scheduling can be determined by the practitioner who is treating any particular patient using his professional skill and knowledge.

A pharmaceutical composition according to the present invention also includes separate compositions comprising a first composition comprising candesartan or a pharmaceutically acceptable salt thereof and a pharmaceutically-acceptable excipient or carrier, and a second composition comprising rosuvastatin or a pharmaceutically acceptable salt thereof and a pharmaceutically-acceptable excipient or carrier. Such a composition conveniently provides the therapeutic combination of the invention for sequential or separate administration in the synergistic prevention or treatment of atherosclerosis but the separate compositions may also be administered simultaneously.

In another aspect of the invention there is provided a combination comprising candesartan, or a pharmaceutically acceptable salt thereof, and rosuvastatin, or a pharmaceutically acceptable salt thereof, for use as a medicament for the prevention or treatment of atherosclerosis.

In another aspect of the invention there is provided a combination comprising candesartan, or a pharmaceutically acceptable salt thereof, and rosuvastatin, or a pharmaceutically acceptable salt thereof, for use as a medicament for the prevention of cardiovascular events.

In another aspect of the invention there is provided a combination comprising candesartan, or a pharmaceutically acceptable salt thereof, and rosuvastatin, or a pharmaceutically acceptable salt thereof, for use in the manufacture of a medicament.

In another aspect of the invention there is provided a combination comprising candesartan, or a pharmaceutically acceptable salt thereof, and rosuvastatin, or a pharmaceutically acceptable salt thereof, for use in the manufacture of a medicament for the prevention or treatment of atherosclerosis.

In another aspect of the invention there is provided a combination comprising candesartan, or a pharmaceutically acceptable salt thereof, and rosuvastatin, or a pharmaceutically acceptable salt thereof, for use in the manufacture of a medicament for the prevention of cardiovascular events.

In a further aspect of the invention there is provided a method of preventing or treating atherosclerosis in a warm-blooded animal, such as man, which comprises administering a combination of candesartan, or a pharmaceutically acceptable salt thereof, and rosuvastatin, or a pharmaceutically acceptable salt thereof.

In a further aspect of the invention there is provided a method of preventing cardiovascular events in a warm-blooded animal, such as man, which comprises administering a combination of candesartan, or a pharmaceutically acceptable salt thereof, and rosuvastatin, or a pharmaceutically acceptable salt thereof.

According to a further aspect of the present invention there is provided a kit comprising a combination of candesartan or a pharmaceutically acceptable salt thereof, and rosuvastatin; or a pharmaceutically acceptable salt thereof optionally with instructions for use in the prevention or treatment of atherosclerosis.

According to a further aspect of the present invention there is provided a kit comprising:
a) candesartan in a first unit dosage form;
b) rosuvastatin in a second unit dosage form; and
c) container means for containing said first and second dosage forms; and optionally
d) with instructions for use in the prevention or treatment of atherosclerosis.

According to another aspect of the present invention there is provided a method of inhibiting expression of CD40 and/or metalloproteinases (MMPs) by administering a combination of candesartan, or a pharmaceutically acceptable salt thereof and rosuvastatin, or a pharmaceutically acceptable salt thereof.

Particular metalloproteinases are MMP-1, MMP-2 and MMP-9.

According to another aspect of the present invention there is provided a method of treating atherosclerotic patients by inhibition of expression of CD40 and/or metalloproteinases (MMPs) by administering an amount of a combination of candesartan, or a pharmaceutically acceptable salt thereof and rosuvastatin, or a pharmaceutically acceptable salt thereof suitable for inhibition of expression of CD40 and/or metalloproteinases (MMPs).

According to a further aspect of the invention, there is provided a method for normalizing the balance between MMPs and TIMPS by administration of an amount of a combination of candesartan, or a pharmaceutically acceptable salt thereof and rosuvastatin, or a pharmaceutically acceptable salt thereof.

According to another aspect of the present invention there is provided a method of inhibiting expression of LOX-1 by administering a combination of candesartan, or a pharmaceutically acceptable salt thereof and rosuvastatin, or a pharmaceutically acceptable salt thereof.

According to another aspect of the present invention there is provided a method of treating atherosclerotic patients by inhibition of expression of LOX-1 by administering an amount of a combination of candesartan, or a pharmaceutically acceptable salt thereof and rosuvastatin, or a pharmaceutically acceptable salt thereof suitable for inhibition of expression of LOX-1.

Materials and Methods
Animal Model

Five pairs of C57BL/6J mice and three pairs of homozygous apo-E knockout mice (on C57BL/6J background) were obtained from Jackson Laboratories (Bar Harbor, Me.). They were bred by brother-sister mating and housed in a room lit from 6:00 AM to 6:00 PM and kept at 21° C. The C57BL/6J mice (n=10) were continued on regular diet for the entire study period. The apo-E knockout mice were divided into four groups. Group 1 (n=10) animals were given high-cholesterol diet (1% cholesterol) alone for 12 weeks since the age of 6 weeks; Group 2 (n=10) animals were given high-cholesterol diet with candesartan (1 mg/kg/d) for 12 weeks since the age of 6 weeks; Group 3 (n=10) animals were given high-cholesterol diet with the rosuvastatin (1 mg/kg/d) for 12 weeks since the age of 6 weeks; Group 4 (n=10) animals were given high-cholesterol diet with candesartan (1 mg/kg/d) and rosuvastatin (1 mg/kg/d) for 12 weeks since the age of 6 weeks.

At the end of 12-week-treatment, the mice were sacrificed and subject to studies described below. All experimental procedures were performed in accordance with protocols approved by the institutional Animal Care and Usage Committee of University of Arkansas for Medical Sciences.

Quantitative Analysis of Atherosclerotic Plaques

At the end of 12-week-treatment, 5 mice from each group were euthanized and the aortas were separated from surrounding tissues. After removal of the adventitial fat tissue, the aortas were opened longitudinally from the aorta arch to the iliac bifurcation, and fixed in 10% formalin for 24 hours. Then the aortas were rinsed in 70% alcohol briefly, stained with Sudan IV solution for 15 minutes, differentiated in 80% alcohol for 20 minutes and washed in running water for 1 hour (Russell L. Techniques for studying atherosclerotic lesion, Lab Invest. 1958; 7:42-47). The aortas were mounted and their pictures were taken with a camera connected to a dissection microscope. The images were analyzed by soft ware (Image Pro Plus, Media Cybernetics).

RNA Preparation and Analysis by RT-PCR

At the end of 12-week-treatment, 5 mice from each group were euthanized and the aortas (from aorta arch to iliac bifurcation) were separated from surrounding tissues and stored on dry ice. Each aorta was cut into four segments, two of which were used to extract total RNA with the single-step acid-guanidinium thiocyanate-phenol-chloroform method as described earlier (27). One microgram of total RNA was reverse transcribed into cDNA with oligo-dT (Promega, Madison, Wis., U.S.A.) and Maloney murine leukemia virus (M-MLV) reverse transcription (Promega) at 42° C. for 1 hour. Two microliters of reverse transcription (RT) material was amplified with Taq DNA polymerase (Promega) and a primer pair specific to mouse LOX-1, CD40 or MIVIPs (-1,-2,-9). For mouse LOX-1, forward primer: 5'-TTACTCTC-CATGGTGGTGCC-3' (SEQ ID NO: 1), reverse primer: 5'-AGCTTCTTCTGCTTGTTGCC-3' (SEQ ID NO: 2) were used. 30 cycles of polymerase chain reaction (PCR) were performed at 94° C. for 40 seconds (denaturation), 55° C. for 1 minute (annealing), and 72° C. for 1 minute (extension). The size of polymerase chain reaction (PCR) product was 193 base pairs. For mouse CD40, forward primer 5'-GTT-TAAAGTCCCGGATGCGA-3' (SEQ ID NO: 3) and reverse primer 5'-CTCAAGGCTATGCTGTCTGT-3' (SEQ ID NO: 4) were used. 35 cycles of polymerase chain reaction (PCR) were performed at 94° C. for 1 minute (denaturation), 55° C. for 1 minute (annealing), and 72° C. for 1 minute (extension). The size of PCR product was 408 base pairs. For mouse MMP-1, forward primer 5'-GGACTCTCCCATTCT-TAATGA T-3' (SEQ ID NO: 5) and reverse primer 5'-CCTCTTTCTGGATAACATCATCA AC-3' (SEQ ID NO: 6) were used. For mouse MMP-2, forward primer 5'-AT-CAAGGGGATCCAGGAGC-3' (SEQ ID NO: 7) and reverse primer 5'-GCAGCGATGAAG ATGATAG-3' (SEQ ID NO:

8) were used. For mouse MMP-9, forward primer 5'-AGTTTGGTGTCGCGGAGCAC-3' (SEQ ID NO: 9) and reverse primer 5'-TACATGAGCGCTTCCGGCAC-3' (SEQ ID NO: 10) were used. For all MMPs, 35 cycles of PCR were performed at 94° C. for 1 minute (denaturation), 58° C. for 1 minute (annealing), and 75° C. for 1 minute (extension). The sizes of PCR product were 627, 718 and 753 base pairs, respectively. A primer pair specific to mouse β-actin was used as housekeeping gene (forward primer: 5'-TTCTA-CAATGAGCTGCGTTG-3' (SEQ ID NO: 11), reverse primer: 5'-CACTGTGTTGGCATAGAGGTC-3' (SEQ ID NO: 12)). 30 cycles were used at 94° C. for 30 seconds (denaturation), 55° C. for 1 minute (annealing), and 72° C. for 1 minute (extension). PCR product was 560 base pairs. The reverse transcription PCR (RT-PCR)-amplified sample was visualized on 1.5% agarose gel using ethidium bromide.

Protein Preparation and Analysis by Western Blot

Each mouse aorta was cut into four segments. Two of them were used to extract RNA, and the remaining two were used to extract protein as described previously (14). In brief, the aortic tissues were homogenized and lysed in lysis buffer, then centrifuged at 4000 rpm for 10 minutes at 4° C. The lysate proteins from aortas (20 µg/lane) were separated by 10% SDS-PAGE, and transferred to nitrocellulose membranes. After incubation in blocking solution (5% non-fat milk, Sigma), membranes were incubated with 1:750 dilution monoclonal antibody to mouse LOX-1, 1:500 dilution polyclonal antibody to mouse CD40 (Santa Cruz), 1 µg/ml dilution monoclonal antibody to mouse MMP-1 (Oncogene), 1 µg/ml dilution monoclonal antibody to mouse MMP-2 (Oncogene). 1 µg/ml dilution monoclonal antibody to mouse MMP-9 (Oncogene), 1:500 dilution polyclonal antibody to mouse TIMP-1 (Santa Cruz), 1:500 dilution polyclonal antibody to mouse TIMP-2 (Santa Cruz), or 1:5000 dilution monoclonal antibody to mouse β-actin (Sigma) for overnight at 4° C. Membranes were washed and then incubated with 1:5000 dilution specific secondary antibody (Amersham Life Science) for 2 hours at room temperature, and the membranes were washed and detected with the ECL system (Amersham Life Science). The relative intensities of protein bands were analyzed by Scan-gel-it software (Li D Y, Zhang Y C, Sawamura T, Mehta J L. Circ Res. 1999; 84:1043-1049).

Data Analysis

All data represent mean of duplicate samples. Data are presented as mean±SD. Statistical significance was determined in multiple comparisons among independent groups of data in which ANOVA and the F test indicated the presence of significant differences. A P value <0.05 was considered significant.

Results

The Synergistic Anti-Atherosclerotic Effect of Candesartan and Rosuvastatin

Compared with the control mice (C57BL/6J mice fed regular diet), the apo-E knockout mice fed high-cholesterol diet developed extensive atherosclerosis (P<0.01 vs control mice). Although both candesartan and rosuvastatin alone decreased the extent of atherosclerosis (p<0.05 vs high-cholesterol diet alone), the combination reduced atherosclerosis to a much greater extent (P<0.05 vs candesartan or rosuvastatin alone plus high-cholesterol diet). FIG. 1 shows results of representative experiments and the extent of atherosclerosis (mean±SD) in different groups of animals.

Figure 2:
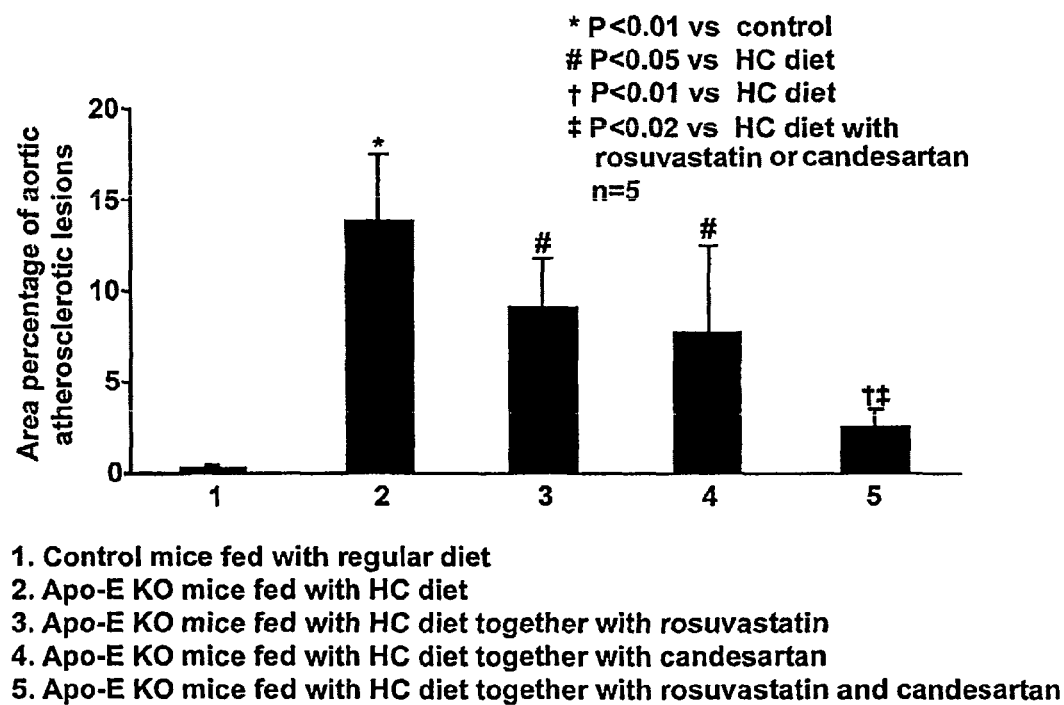
FIG. 2 graphically illustrates the area percentage of aortic atherosclerotic lesions from representative comparative experiments using control mice fed with a regular diet and apo-E knockout mice fed with a high cholesterol diet, or a high cholesterol diet and administered candesartan or rosuvastatin or a combination of candesartan and rosuvastatin.

Candersartan and rosuvastatin alone decreased atherosclerosis by about 35% and 25% respectively. The combination reduced atherosclerosis by 70%, demonstrating a synergistic effect. This effect is illustrated graphically in FIG. 2.

The Synergistic Effect of Candesartan and Rosuvastatin on LOX-1 Expression

In the control C57BL/6J mice, the expression of LOX-1 (mRNA and protein) was low. In contrast. LOX-1 expression (mRNA and protein) was markedly increased by high-cholesterol diet in apo-E knockout mice (P<0.01 vs control mice). Both candesartan and rosuvastatin alone decreased the LOX-1 expression (mRNA and protein), albeit modestly (P<0.05 vs high-cholesterol diet alone). The combination of candesartan and rosuvastatin had a dramatic inhibitory effect on the up-regulation of LOX-1 (mRNA and protein) in apo-E knockout mice (P<0.01 vs high-cholesterol diet alone).

The Synergistic Effect of Candesartan and Rosuvastatin on CD40 Expression

Compared with the expression in control C57BL/6J mice, CD40 expression (mRNA and protein) was markedly increased in apo-E knockout mice fed a high-cholesterol diet in (P<0.01 vs control mice). Although candesartan and rosuvastatin treatment alone slightly decreased CD40 expression (P<0.05 vs high-cholesterol diet alone), the combination of candesartan and rosuvastatin had a dramatic inhibitory effect on the up-regulation of CD40 (mRNA and protein) in the apo-E knockout mice (P<0.01 vs high-cholesterol diet alone).

The Synergistic Effect of Candesartan and Rosuvastatin on Mmps Expression

Compared with the expression in control C57BL/6J mice, MMP-1, -2 and -9 expression (mRNA and protein) was markedly increased in high-cholesterol diet-fed apo-E knockout mice (P<0.01 vs control mice). Both candesartan and rosuvastatin alone decreased MMP-1, -2 and -9 expression (mRNA and protein), albeit modestly (P<0.05 vs high-cholesterol diet alone). The combination of candesartan and rosuvastatin had a dramatic inhibitory effect on their expression (P<0.01 vs high-cholesterol diet alone).

The Effect of Candesartan and Rosuvastatin on TIMPS Expression

TIMP-1 and TIMP-2 protein expression was also increased in apo-E knockout mice by high-cholesterol diet (P<0.01 vs. control mice), but the increase was less than that of MMPs. Both candesartan and rosuvastatin alone reduced TIMP-1 and TIMP-2 expression by a small degree (P<0.05 vs. high-cholesterol diet alone), but the combination of candesartan and rosuvastatin had a greater inhibitory effect on their expression (P<0.01 vs. high-cholesterol diet alone, P<0.05 vs. high-cholesterol diet with candesartan or rosuvastatin).

The invention claimed is:

1. A method of treating or reducing the extent of atherosclerosis in a warm-blooded animal in need thereof, which comprises administering to said animal an effective amount of a combination consisting essentially of candesartan or a pharmaceutically acceptable salt thereof and rosuvastatin or a pharmaceutically acceptable salt thereof as the sole therapeutically effective agents, and optionally a diuretic which is hydrochlorothiazide.

2. The method of claim 1 wherein the composition is in the form of a single oral formulation.

3. The method of claim 1 or claim 2 wherein the composition is administered in association with a pharmaceutically acceptable diluent or carrier.

4. The method of claim 1 or claim 2 wherein candesartan is administered in the form of candesartan cilexetil.

5. The method of claim 3 wherein candesartan is administered in the form of candesartan cilexetil.

* * * * *